(12) United States Patent
Wei et al.

(10) Patent No.: US 12,402,800 B2
(45) Date of Patent: Sep. 2, 2025

(54) HEART RATE DETECTION MODULE AND ELECTRONIC DEVICE

(71) Applicant: Huawei Technologies Co., Ltd., Shenzhen (CN)

(72) Inventors: Wenxiong Wei, Hangzhou (CN); Xingxing Chen, Shanghai (CN); Minli Chen, Dongguan (CN); Bing Wu, Dongguan (CN); Fan Wang, Shenzhen (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 160 days.

(21) Appl. No.: 18/557,018

(22) PCT Filed: Apr. 19, 2022

(86) PCT No.: PCT/CN2022/087591
§ 371 (c)(1),
(2) Date: Oct. 24, 2023

(87) PCT Pub. No.: WO2022/228197
PCT Pub. Date: Nov. 3, 2022

(65) Prior Publication Data
US 2024/0206750 A1 Jun. 27, 2024

(30) Foreign Application Priority Data
Apr. 25, 2021 (CN) .......................... 202110449802.0

(51) Int. Cl.
*A61B 5/024* (2006.01)
*A61B 5/00* (2006.01)
*A61B 5/1455* (2006.01)

(52) U.S. Cl.
CPC ........ *A61B 5/02416* (2013.01); *A61B 5/1455* (2013.01); *A61B 5/725* (2013.01)

(58) Field of Classification Search
CPC .... A61B 5/02416; A61B 5/1455; A61B 5/725
(Continued)

(56) References Cited

U.S. PATENT DOCUMENTS

2015/0141774 A1* 5/2015 Ogawa ................. A61B 5/6817
600/521
2015/0148681 A1* 5/2015 Abreu .................. A61B 5/6821
600/474

(Continued)

FOREIGN PATENT DOCUMENTS

| CN | 109414225 A | 3/2019 |
| CN | 208689385 U | 4/2019 |

(Continued)

OTHER PUBLICATIONS

Chung Shuang-Chao et al: "Signal-enhancement reflective pulse Oximeter with Fresnel lens", Optics Communications, Elsevier, Amsterdam, NL, [Online] vol. 375, May 5, 2016 (May 5, 2016), XP029554481, pp. 9-14.

(Continued)

*Primary Examiner* — Md M Rahman
(74) *Attorney, Agent, or Firm* — Slater Matsil, LLP

(57) ABSTRACT

A heart rate detection module and an electronic device are disclosed. The heart rate detection module includes a substrate, and a light source, an optical receiver, a light blocking portion, and an optical film that are disposed on the substrate. The light blocking portion is disposed between the light source and the optical receiver, so that the light source is optically isolated from the optical receiver. The optical film covers the light source, the light blocking portion, and the optical receiver, and a light filtering portion is disposed on a side that is of the optical film and that faces the substrate.

20 Claims, 13 Drawing Sheets

(58) Field of Classification Search
USPC .......................................................... 356/432
See application file for complete search history.

(56) References Cited

U.S. PATENT DOCUMENTS

| | | |
|---|---|---|
| 2016/0058312 A1 | 3/2016 | Han et al. |
| 2017/0164848 A1 | 6/2017 | Nadeau et al. |
| 2018/0228414 A1 | 8/2018 | Shao et al. |
| 2019/0324593 A1 | 10/2019 | Chung et al. |

FOREIGN PATENT DOCUMENTS

| | | |
|---|---|---|
| WO | 2020194036 A1 | 10/2020 |
| WO | 2021041961 A1 | 3/2021 |

OTHER PUBLICATIONS

Hwang Chan-Sol et al: "Angle-selective Optical filter for highly sensitive reflection photoplethysmogram", Biomedical Optics Express, [Online] vol. 8, No. 10, Sep. 7, 2017 (Sep. 7, 2017), XP093195864, total 8 pages.

* cited by examiner

HEART RATE DETECTION MODULE AND ELECTRONIC DEVICE

CROSS-REFERENCE TO RELATED APPLICATIONS

This application is a National Stage of International Patent Application No. PCT/CN2022/087591 filed on Apr. 19, 2022, which claims priority to Chinese Patent Application No. 202110449802.0 filed on Apr. 25, 2021. Both of the aforementioned applications are hereby incorporated by reference in their entireties.

TECHNICAL FIELD

This application relates to the technical field of electronic devices, and in particular, to a heart rate detection module and an electronic device.

BACKGROUND

As people pay more attention to their own health, various simple and convenient electronic device technologies emerge.

Currently, an electronic device (such as a wearable device or a small heart rate meter) for detecting a heart rate mainly uses a photoplethysmograph (Photoplethysmograph, PPG) technology. FIG. 1 is a diagram of a principle of applying a PPG technology to heart rate detection. When the heart beats, blood vessels in a human body contract and expand accordingly, resulting in a change in a blood volume (for example, pulsating blood 01 shown in FIG. 1), and the change causes different degrees of absorption impact on light. Therefore, according to the PPG technology, a specific light beam is used to irradiate skin, and reflected light is analyzed according to the phenomenon, to obtain a heart rate value of the human body.

Different from professional medical detection, a detection result obtained from the foregoing electronic device is usually used as a reference by a user to manage heart health in daily life. However, with popularity of such electronic devices and higher requirements of people on heart rate detection, how to increase heart rate detection accuracy of such electronic devices becomes an urgent problem to be resolved.

SUMMARY

This application provides a heart rate detection module and an electronic device, to filter interference light generated in a heart rate detection process, thereby increasing heart rate detection accuracy.

According to a first aspect, this application provides a heart rate detection module. The heart rate detection module includes a substrate, where a light source is disposed on the substrate, and the light source emits a light beam used for heart rate detection; an optical receiver disposed at an interval from the light source, where the optical receiver is configured to receive an optical signal; a light blocking portion located between the light source and the optical receiver, where the light blocking portion may optically isolate the light source from the optical receiver, so that the light beam emitted from the light source cannot directly radiate the optical receiver; and an optical film covering the light source, the optical receiver, and the light blocking portion, where a light filtering portion is disposed on a side that is of the optical film and that is close to the substrate, and the light filtering portion may filter, in a heart rate detection process, interference light emitted to the optical receiver, to increase a signal-to-noise ratio of the heart rate detection module, thereby implementing relatively high heart rate detection accuracy.

The light filtering portion may include a first light guide portion. The first light guide portion is disposed close to the light source, and is configured to guide, to deviate from the optical receiver, interference light emitted from the light source, to reduce interference light received by the optical receiver, thereby increasing a signal-to-noise ratio of the optical signal received by the optical receiver.

In a specific technical solution, the first light guide portion may be disposed in a manner that a section that is of the first light guide portion and that is along a direction perpendicular to the optical film is a triangle, and meets: $x1 > y1$, where $x1$ is a length of a projection, on a surface of the optical film, of a side edge that is of the triangle section and that is close to the light source, and $y1$ is a length of a projection, on the surface of the optical film, of a side edge that is of the triangle section and that is away from the light source. Compared with a surface of a flat optical film, the first light guide portion changes an optical path of the interference light from the light source, so that the interference light deviates from the optical receiver, to reduce the interference light emitted to the optical receiver.

To more effectively filter the interference light from the light source, the first light guide portion may meet: $60\% \leq x1/(x1+y1) \leq 85\%$.

To make the first light guide portion easy to manufacture and process while a good light filtering effect of the first light guide portion is maintained, a height $h1$ of the section of the first light guide portion may meet: $20\,\mu m \leq h1 \leq 40\,\mu m$ and $20\,\mu m \leq x1+y1 \leq 50\,\mu m$.

The light filtering portion may include a second light guide portion. The second light guide portion is disposed close to the optical receiver, and is configured to guide, to deviate from the optical receiver, the interference light emitted from the optical film, to reduce interference light received by the optical receiver, thereby increasing the signal-to-noise ratio of the optical signal received by the optical receiver.

In a specific technical solution, a section that is of the second light guide portion and that is along the direction perpendicular to the optical film is a triangle, and meets: $x2 < y2$, where $x2$ is a length of a projection, on the surface of the optical film, of a side edge that is of the triangle section and that is away from the optical receiver, and $y2$ is a length of a projection, on the surface of the optical film, of a side edge that is of the triangle section and that is close to the optical receiver. Compared with a surface of a flat optical film, the second light guide portion changes an optical path of the interference light emitted from the optical film, so that the interference light deviates from the optical receiver, to reduce the interference light emitted to the optical receiver.

To more effectively filter the interference light emitted from the optical film, the second light guide portion may meet: $15\% \leq x2/(x2+y2) \leq 40\%$.

To make the second light guide portion easy to manufacture and process while a good light filtering effect of the second light guide portion is maintained, a height $h1$ of the section of the second light guide portion may meet: $20\,\mu m \leq h2 \leq 40\,\mu m$ and $20\,\mu m \leq x2+y2 \leq 50\,\mu m$.

The light filtering portion may include a third light guide portion, the third light guide portion is disposed close to the optical receiver, a section that is of the third light guide portion and that is along the direction perpendicular to the optical film is a right triangle, and an internal angle θ that is of the right triangle section and that is away from the optical receiver meets: $5°≤θ≤30°$. Compared with a surface of a flat optical film, the third light guide portion changes an optical path of the interference light emitted to the optical receiver through the optical film, so that the interference light deviates from the optical receiver, to reduce the interference light emitted to the optical receiver.

To make the third light guide portion easy to manufacture and process while a good light filtering effect of the third light guide portion is maintained, a length d3 of an edge of a contact surface between the section of the third light guide portion and the optical film meets: $20 \mu m ≤ d3 ≤ 50 \mu m$.

To further filter the interference light, a light shield layer may be disposed on the surface of the optical film, and the light shield layer corresponds to the light blocking portion, to avoid affecting a light beam used for heart rate detection.

The optical film may be an entire optical film, to simplify a structure and an assembly procedure of the heart rate detection module.

In a specific technical solution, the light source, the light blocking portion, and the optical receiver may be integrally packaged, to implement a relatively thin heart rate detection module.

According to a second aspect, this application provides an electronic device, where the electronic device includes an electronic device body and the heart rate detection module in any one of the foregoing technical solutions, and the heart rate detection module is configured to obtain a heart rate signal of a user. In a process of obtaining an optical signal, a light filtering portion may filter interference light emitted to an optical receiver, to increase a signal-to-noise ratio of the obtained heart rate signal, thereby implementing heart rate detection with relatively high accuracy.

In a specific technical solution, the heart rate detection module is detachably connected to the electronic device body, to facilitate maintenance of the electronic device and replacement of the heart rate detection module.

REFERENCE NUMERALS

In the Background:
    01—pulsating blood; 02—arterial non-pulsating blood; 03—vein blood; 04—skin surface layer;
in embodiments of this application:
    10—heart rate detection module; 20: electronic device; 30—detection part; 11—substrate; 12—light source; 13—optical receiver; 14—light blocking portion; 15—optical film; 150—light filtering portion; 151—first light guide portion; 152—second light guide portion; 153—third light guide portion; 16—light shield layer; 17—cover; 18—packaging layer.

DETAILED DESCRIPTION OF ILLUSTRATIVE EMBODIMENTS

To make objectives, technical solutions, and advantages of this application clearer, the following further describes this application in detail with reference to the accompanying drawings.

As electronic device technologies develop, a growing quantity of functions are added to electronic devices to meet different requirements of users. For example, a smartwatch favored by consumers in recent years not only has a function of a conventional watch, for example, displaying a time and a date, but also may monitor information about an activity of a user, such as walking, swimming, running, or cycling, thereby facilitating daily health management of the user. Particularly, to help the user monitor a heart rate status of the user in daily life or during exercise, a growing quantity of electronic devices have a heart rate detection module configured to detect a heart rate of the user. The heart rate detection module obtains heart rate data of the user by using a PPG technology. The heart rate data may be used to monitor a daily heart rate status of the user, warn an abnormal heart rate (for example, an irregular, excessively fast, or excessively slow heartbeat), and the like.

Figure 1:
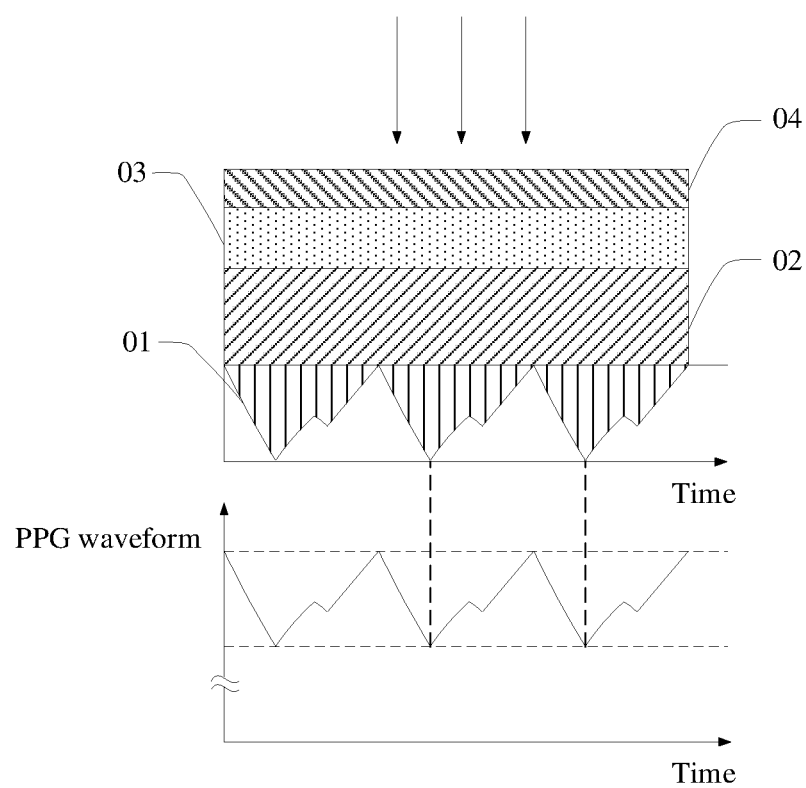
FIG. 1 is a schematic diagram of a principle of applying a PPG technology to heart rate detection.

However, currently, when the user detects a heart rate by using an electronic device, accuracy of a heart rate signal obtained by the heart rate detection module is not high. In other words, an error exists between the heart rate reflected by the data and a real heart rate. This is because when the heart rate detection module receives light (referred to as "effective light" in this application) reflected by pulsating blood 01, the heart rate detection module further receives light reflected from another tissue (such as arterial non-pulsating blood 02, vein blood 03, and a skin surface layer 04 that are shown in FIG. 1), light reflected from a component of the electronic device, or the like. The light beams (which may be referred to as interference light in this application) interfere with analysis performed by the electronic device on the effective light to some extent. Consequently, reliability of the heart rate data obtained by the electronic device is poor, and accuracy of a finally obtained heart rate detection result is not high.

Therefore, this application provides a heart rate detection module and an electronic device, to filter interference light generated in a heart rate detection process, thereby increasing heart rate detection accuracy.

Figure 2:
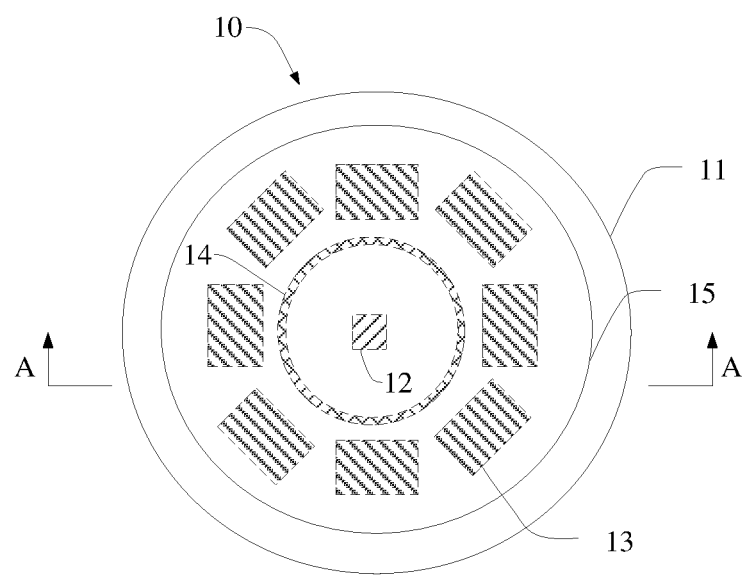
FIG. 2 is a schematic diagram of a structure of a heart rate detection module according to an embodiment of this application.
Figure 3:
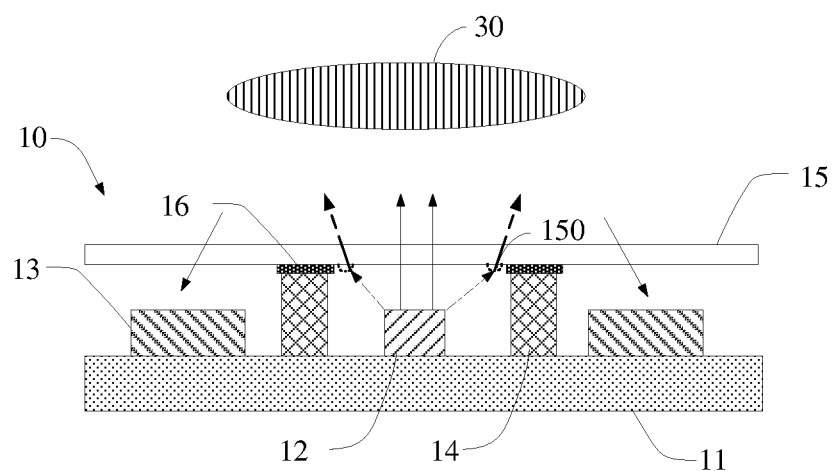
FIG. 3 is a schematic sectional view of a heart rate detection module along a direction A-A in FIG. 2.

FIG. 2 is a schematic diagram of a structure of a heart rate detection module 10 according to an embodiment of this application. FIG. 3 is a schematic sectional view of a heart rate detection module 10 along a direction A-A in FIG. 2. The heart rate detection module 10 provided in this application includes a substrate 11, one or more light sources 12, one or more optical receivers 13, one or more light blocking portions 14, and an optical film 15 that are disposed on the substrate 11. As shown in FIG. 2 and FIG. 3, in this embodiment, the heart rate detection module 10 includes one light source 12, eight optical receivers 13, and one light blocking portion 14. Specifically, the light source 12 is disposed at an interval from each optical receiver 13. The light blocking portion 14 is disposed between the light source 12 and each optical receiver 13, and is configured to optically isolate the light source 12 from each optical receiver 13, so that a light beam emitted by the light source 12 cannot directly irradiate each optical receiver 13, in other words, the light beam emitted from the light source 12 can reach each optical receiver 13 only after being refracted and/or reflected by another light transmission device (for example, the optical film 15) of the heart rate detection module 10. The optical film 15 covers the light source 12, the optical receivers 13, and the light blocking portion 14 (as shown in FIG. 2). In other words, the light source 12, the optical receivers 13, and the light blocking portion 14 are located between the substrate 11 and the optical film 15 (as shown in FIG. 3). A light filtering portion 150 (represented by a dashed line in FIG. 3) is disposed on a side that is of the optical film 15 and that faces the substrate 11, and the light filtering portion 150 may filter interference light emitted to each optical receiver 13. It should be noted that the light filtering portion 150 in FIG. 3 is merely a schematic diagram, and is not used to limit a quantity of light filtering portions 150, a structure of the light filtering portion 150, and a location between the light filtering portion 150 and another component. The "filtering interference light" described in this application may mean absorbing the interference light, or may mean that all or some of the interference light cannot reach the optical receiver 13 after the interference light is reflected and/or refracted.

During application, the heart rate detection module 10 is put close to a detection part 30 of a user. In this case, a side that is of the optical film 15 and that is away from the substrate 11 is close to the detection part 30. It should be noted that the "detection part" described in this application is a body part from which a heart rate signal can be detected, and may be a part close to a heart, for example, a chest, or may be a part away from a heart, such as a neck, a wrist, a fingertip, or a foot. When a heart rate is to be detected, the light source 12 emits a light beam used for heart rate detection. After passing through the optical film 15, the light beam is reflected at the detection part 30. The reflected light beam passes through the optical film 15 again and reaches each optical receiver 13 (as shown by a solid arrow in FIG. 3). However, interference light generated in the process is filtered by the light filtering portion 150 (as shown by a dashed arrow in FIG. 3). An electronic device analyzes an optical signal received by each optical receiver 13, so that heart rate data of the user can be obtained. In this embodiment of this application, after the interference light is filtered, a proportion of effective light received by the one or more optical receivers 13 is increased, and the heart rate detection module 10 may obtain a relatively high signal-to-noise ratio, so that heart rate detection accuracy can be well increased.

Figure 4:
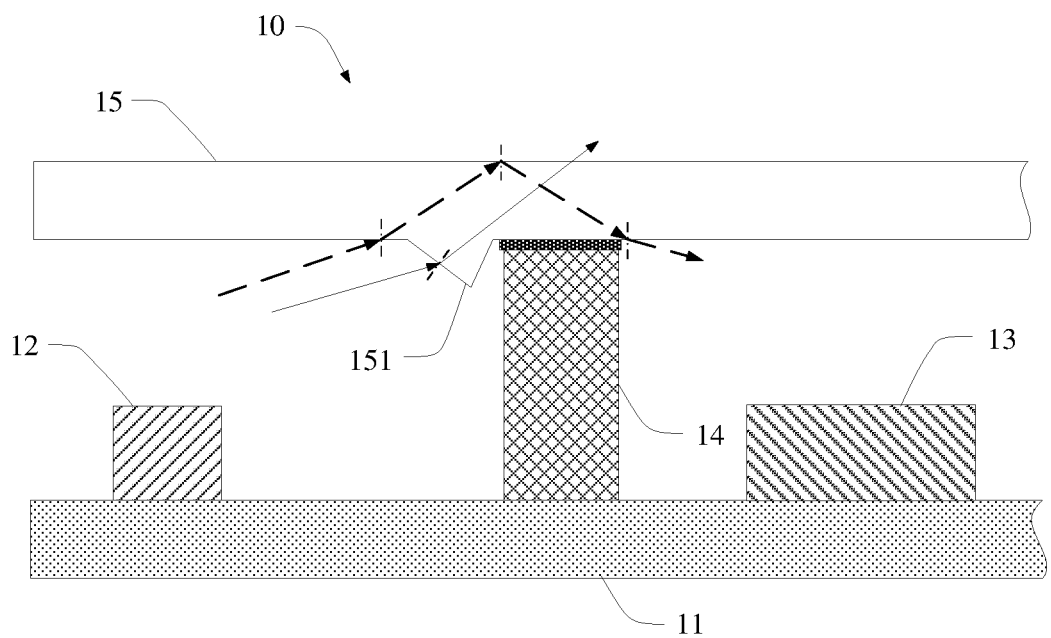
FIG. 4 is a locally enlarged schematic diagram of a heart rate detection module according to an embodiment of this application.

The following describes a structure of the foregoing optical film 15 in detail. FIG. 4 is a locally enlarged schematic diagram of a heart rate detection module 10 according to an embodiment of this application. As shown in FIG. 4, for example, the heart rate detection module 10 includes one light source 12, one optical receivers 13, and one light blocking portion 14. In this embodiment, one light filtering portion 150 is disposed on the optical film 15. The light filtering portion 150 includes one first light guide portion 151. The first light guide portion 151 is close to the light source 12. That is, the first light guide portion 151 is located on a side that is of the light blocking portion 14 and that faces the light source 12. The first light guide portion 151 is configured to guide, in a direction deviating from the optical receiver 13, interference light that comes from the light source 12. Specifically, FIG. 4 is a schematic diagram of a path, shown by using dashed arrows, of a light beam passing through the optical film 15 in a current technology. Some light beams emitted from the light source 12 are refracted on a surface that is of the optical film 15 and that faces a substrate 11, some of refracted light is totally reflected in the optical film 15, and the totally reflected light reaches the optical receiver 13 after being emitted from the optical film 15. In other words, after being emitted from the light source 12, the some of light is emitted into the optical film 15, is totally reflected in the optical film 15, and is then emitted to the optical receiver 13, to form interference light. In the current technology, such interference light causes a decrease in a proportion of effective light in an optical signal received by the optical receiver 13. In FIG. 4, a light beam (on a right side of the light beam shown by the dashed arrows) shown by solid arrows is a schematic diagram of a path of the light beam (that is, the light beam shown by the dashed arrows) in the current technology in this embodiment. Apparently, compared with the current technology, under an action of the first light guide portion 151 in this embodiment, a refraction path of the light beam changes, so that the light beam cannot be totally reflected in the optical film 15, but is emitted from a surface of a side that is of the optical film 15 and that is away from the substrate 11. In this way, the light beam deviates from the optical receiver 13, to reduce interference to the optical receiver 13.

As shown in FIG. 4 again, among the light beams emitted from the light source 12, only a light beam with a relatively large incident angle may be totally reflected after being emitted into the optical film 15, and is finally emitted to the optical receiver 13 after being refracted from the surface that is of the optical film 15 and that faces the substrate 11. Therefore, as shown in FIG. 4, in some specific embodiments of this application, a section that is of the first light guide portion 151 and that is along a direction perpendicular to the optical film 15 (as shown in FIG. 4, a plane in which the section of the first light guide portion 151 is located is perpendicular to the optical film 15) may be set to a triangle.

Figure 5:
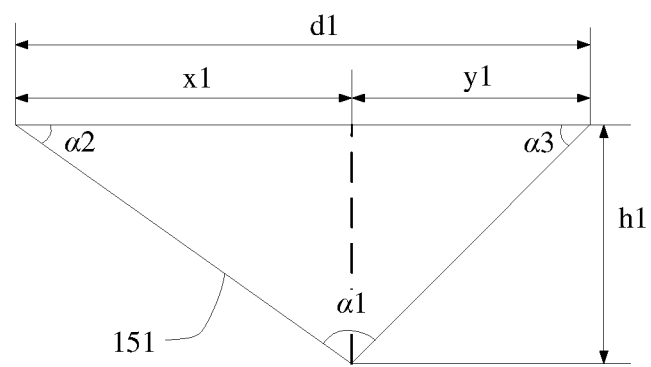
FIG. 5 is a schematic sectional view of a first light guide portion according to an embodiment of this application.

FIG. 5 is a schematic sectional view of a first light guide portion 151 according to an embodiment of this application. It should be noted that, in this embodiment of this application, for ease of description, orientation terms such as upper, lower, left, right, top, and bottom are introduced. The orientation terms are merely used to more briefly describe and help a reader locate a described object in a figure, but do not specifically limit a location and a direction of the object.

In a section shown in FIG. 5, a vertex angle $\alpha 1$ (an angle away from the optical film 15) of a triangle is downward, an edge opposite to the vertex angle $\alpha 1$ is referred to as a bottom edge, a side edge on a left side of a dashed line is close to the light source 12 (or is away from an adjacent optical receiver 13), a length of a projection of the side edge on the bottom edge is x1, a side edge on a right side of the dashed line is away from the light source 12 (or is close to the adjacent optical receiver 13), and a length of a projection of the side edge on the bottom edge is y1. In the solution, the first light guide portion 151 may meet: x1>y1, that is, an angle of a left base angle $\alpha 2$ is less than an angle of a right base angle $\alpha 3$. In this way, all or some of interference light emitted into the optical film 15 at a relatively large incident angle after being emitted from the light source 12 may deviate from each optical receiver 13, and is emitted from the surface of the side that is of the optical film 15 and that is away from the substrate 11, thereby reducing interference light emitted to each optical receiver 13, and relatively well increasing a signal-to-noise ratio of the heart rate detection module 10. It should be noted that the "relatively large incident angle" in this application means that an incident angle of interference light is greater than an incident angle of effective light at an interface on which reflection and refraction occur.

A length of a projection of a width of the first light guide portion 151 on the optical film 15 is a length d1 of a bottom edge shown in FIG. 5, where d1=x1+y1 and d1 may meet: 20 μm≤d1≤50 μm. A height h1 of the first light guide portion 151 is a vertical distance h1 from the vertex angle $\alpha 1$ to the bottom edge shown in FIG. 5, and h1 may meet: 20 μm≤h1≤40 μm. In this way, the first light guide portion 151 not only may have a strong function of filtering interference light, in other words, a filtering effect is good, but also is easy to manufacture and process. Certainly, the foregoing width and height may alternatively go beyond the foregoing ranges. However, this may make manufacturing and processing more difficult, or make the effect of filtering interference light not good enough. For example, an excessively large width or an excessively small height of the first light guide portion 151 may cause the first light guide portion 151 to be relatively flat. Consequently, some of light that is emitted into the optical film 15 at a relatively large incident angle may still be emitted to each optical receiver 13 after being totally reflected in the optical film 15, and a filtering function of the first light guide portion 151 declines. For another example, an excessively small width of the first light guide portion 151 may cause a relatively high requirement on manufacturing accuracy of the first light guide portion 151, and manufacturing difficulty and costs are increased.

In some other embodiments, the first light guide portion 151 may further meet 60%≤x1/(x1+y1)≤85%, and a proportion of x1 in the total width d1 falls within a range of 60% to 85% (including the end values), for example, may be 60%, 63.33%, 66.67%, 70%, 73.33%, 77%, 80%, 84%, or 85%. The first light guide portion 151 that meets the range may have a better effect of filtering interference light.

Figure 6:
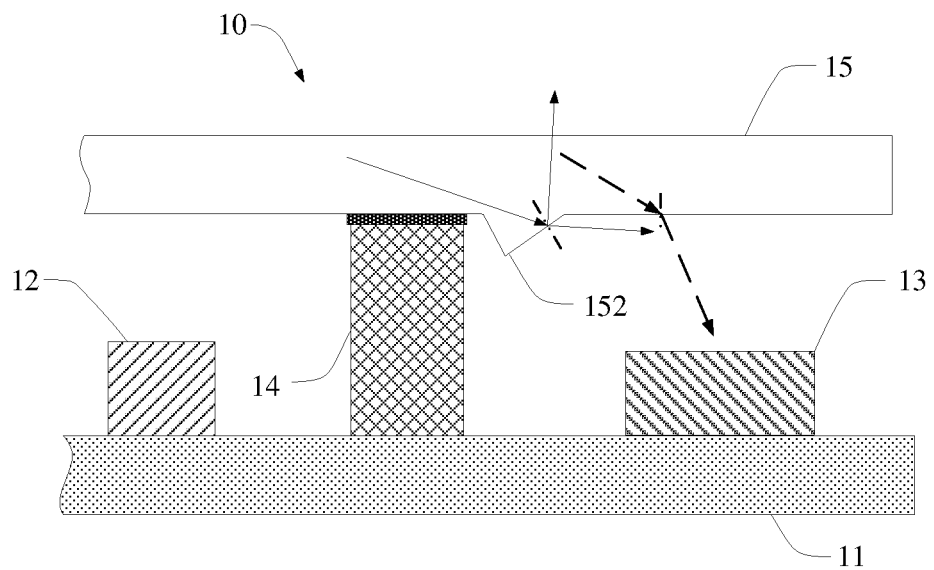
FIG. 6 is another locally enlarged schematic diagram of a heart rate detection module according to an embodiment of this application.

FIG. 6 is another locally enlarged schematic diagram of a heart rate detection module 10 according to an embodiment of this application. As shown in FIG. 6, for example, the heart rate detection module 10 includes one light source 12, one optical receivers 13, and one light blocking portion 14. In this embodiment, one light filtering portion 150 is disposed on the optical film 15. The light filtering portion 150 includes one second light guide portion 152. The second light guide portion 152 is close to the optical receiver 13. That is, the second light guide portion 152 is located on a side that is of the light blocking portion 14 and that is close to the optical receiver 13. The second light guide portion 152 is configured to guide, in a direction deviating from the optical receiver 13, interference light that passes through the optical film 15. Specifically, FIG. 6 is a schematic diagram of another path, shown by using dashed arrows, of a light beam in the optical film 15 in a current technology. Some light beams emitted from the light source 12 are refracted on a surface that is of the optical film 15 and that faces a substrate 11, some of refracted light is totally reflected in the optical film 15, and the totally reflected light reaches the optical receiver 13 after being emitted from the optical film 15, to form interference light. After passing through the optical film 15, the other refracted light is emitted to a detection part 30. After passing through the optical film 15, light reflected by another tissue of the detection part 30 is emitted to the optical receiver 13. In this way, interference light may also be formed. In other words, in addition to effective light, light received by the optical receiver 13 includes the light reflected from the another tissue, and the light that is emitted from the light source 12 into the optical film 15, is reflected in the optical film 15, and is then emitted to the optical receiver 13. The interference light affects a proportion of effective light in an optical signal received by the optical receiver 13. In FIG. 6, a light beam (on a left side of the light beam shown by the dashed arrows) shown by solid arrows is a schematic diagram of a path of the light beam (that is, the light beam shown by the dashed arrows) in a current technology in this embodiment. Apparently, compared with the current technology, under an action of the second light guide portion 152 in this embodiment, a path of the light beam changes, so that the light beam is emitted from a surface of a side that is of the optical film 15 and that is away from the substrate 11, or the light beam is emitted from a surface of a side that is of the optical film 15 and that is close to the substrate 11 and deviates from the optical receiver 13. In this case, the light beam is not received by the optical receiver 13, that is, the light beam cannot reach the optical receiver 13, and interference to the optical receiver 13 may be reduced.

Figure 7:
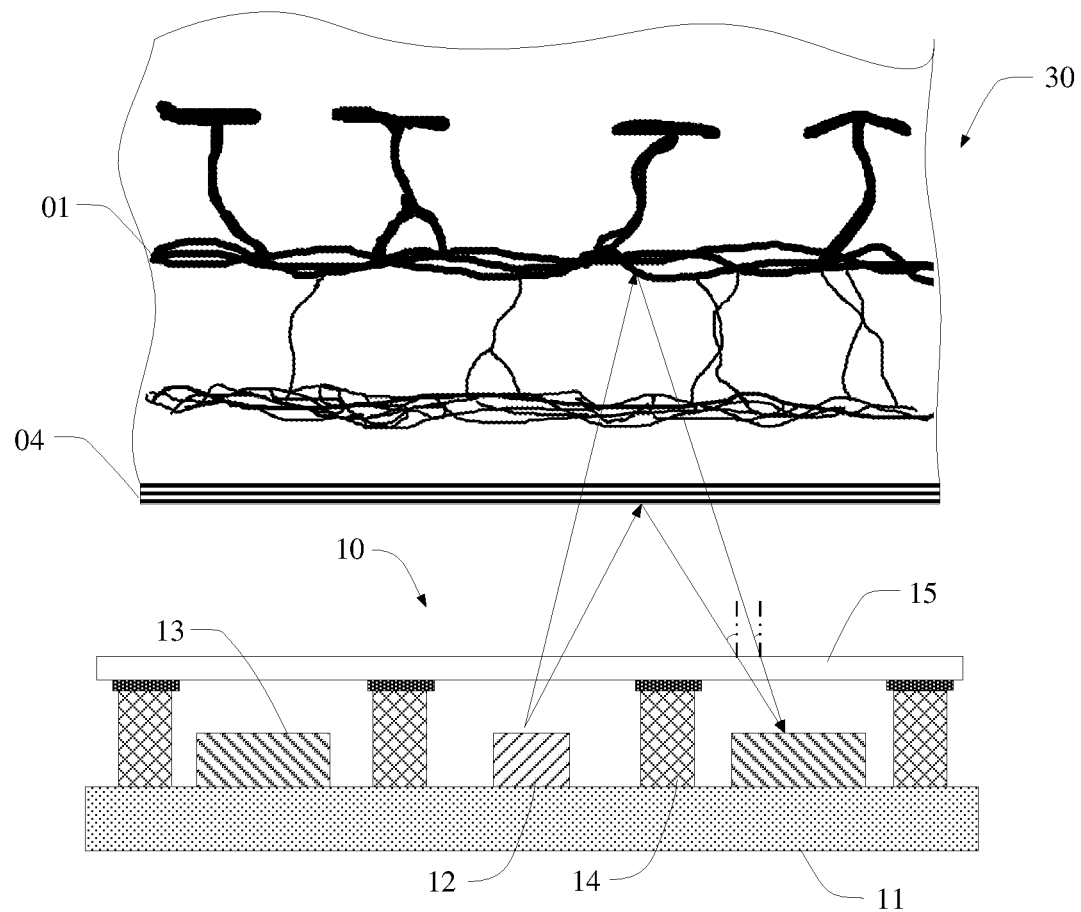
FIG. 7 is a schematic diagram in which a heart rate detection module is configured to detect a heart rate according to an embodiment of this application.

As shown in FIG. 7, because another tissue of the detection part 30 is closer to the heart rate detection module 10 than pulsating blood 01, compared with effective light reflected from the pulsating blood 01, interference light reflected from the another tissue is emitted into the optical film 15 at a larger incident angle. In addition, interference light emitted to each optical receiver 13 after being reflected in the optical film 15 is also emitted, at a relatively large incident angle, to the surface of the side that is of the optical film 15 and that faces the substrate 11. Therefore, as shown in FIG. 6, in some specific embodiments of this application, a section that is of the second light guide portion 152 and that is along a direction perpendicular to the optical film 15 may be set to a triangle.

Figure 8:
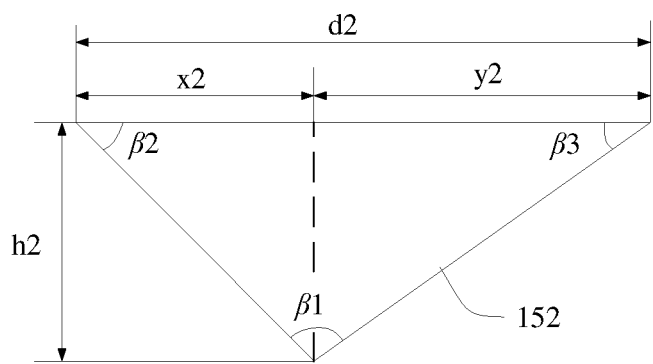
FIG. 8 is a schematic sectional view of a second light guide portion according to an embodiment of this application.

FIG. 8 is a schematic sectional view of a second light guide portion 152 according to an embodiment of this application. In a section shown in FIG. 8, a vertex angle β1 of a triangle is downward, an edge opposite to the vertex angle β1 is referred to as a bottom edge, a side edge on a left side of a dashed line is away from an adjacent optical receiver 13 (or is close to the light source 12), a length of a projection of the side edge on the bottom edge is x2, a side edge on a right side of the dashed line is close to the adjacent optical receiver 13 (or is away from the light source 12), and a length of a projection of the side edge on the bottom edge is y2. In this embodiment of this application, the second light guide portion 152 may meet: x2<y2, that is, an angle of a left base angle β2 is greater than an angle of a right base angle β3. In this way, all or some of interference light emitted from the detection part 30 into the optical film 15 at a relatively large incident angle, and interference light emitted to each optical receiver 13 after being totally reflected in the optical film 15 deviates from the optical receiver 13, thereby reducing interference light emitted to each optical receiver 13, so that a signal-to-noise ratio of the heart rate detection module 10 can be well increased.

A length of a projection of a width of the second light guide portion 152 on the optical film 15 is a length d2 of a bottom edge shown in FIG. 8, where d2=x2+y2 and d2 may meet: 20 µm≤d2≤50 µm. A height h2 of the second light guide portion 152 is a vertical distance h2 from the vertex angle β1 to the bottom edge shown in FIG. 8, and h2 may meet: 20 µm≤h2≤40 µm. In this way, the second light guide portion 152 not only may have a strong function of filtering interference light, in other words, a filtering effect is good, but also is easy to manufacture and process. Certainly, the foregoing width and height may alternatively go beyond the foregoing ranges. However, this may make manufacturing and processing more difficult, or make the effect of filtering interference light not good enough. For example, an excessively large width or an excessively small height of the second light guide portion 152 may cause the second light guide portion 152 to be relatively flat. Consequently, some of the light that is emitted, at a relatively large incident angle, to the surface of the side that is of the optical film 15 and that faces the substrate 11 may still be emitted to each optical receiver 13, and a filtering function of the second light guide portion 152 declines. For another example, an excessively small width of the second light guide portion 152 may cause a relatively high requirement on manufacturing accuracy of the second light guide portion 152, and manufacturing difficulty and costs are increased.

In some other embodiments, the second light guide portion 152 may further meet 15%≤x2/(x2+y2)≤40%, and a proportion of x2 in the total width d2 falls within a range of 15% to 40% (including the end values), for example, may be 15%, 16%, 20%, 23%, 26.67%, 30%, 33.33%, 36.67, or 40%. The second light guide portion 152 that meets the range may have a better effect of filtering interference light.

Figure 9:
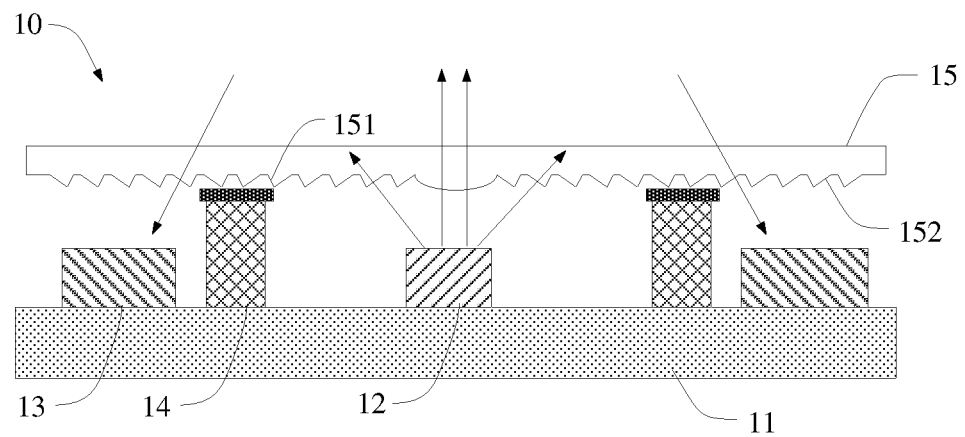
FIG. 9 is a schematic diagram of another sectional structure of a heart rate detection module according to an embodiment of this application.

One embodiment of this application is used below for description. FIG. 9 is a schematic diagram of another sectional structure of a heart rate detection module 10 according to an embodiment of this application. As shown in FIG. 9, a light filtering portion 150 of an optical film 15 includes a plurality of first light guide portions 151 and a plurality of second light guide portions 152. Specifically, both sections that are of the first light guide portion 151 and the second light guide portion 152 and that are along a direction perpendicular to the optical film 15 are set to triangles (referring to schematic sectional views shown in FIG. 5 and FIG. 8), the first light guide portion 151 meets: x1>y1, and the second light guide portion 152 meets: x2<y2. Therefore, as shown in FIG. 9, both a vertex angle of the first light guide portion 151 and a vertex angle of the second light guide portion 152 face a light blocking portion 14.

Figure 10:
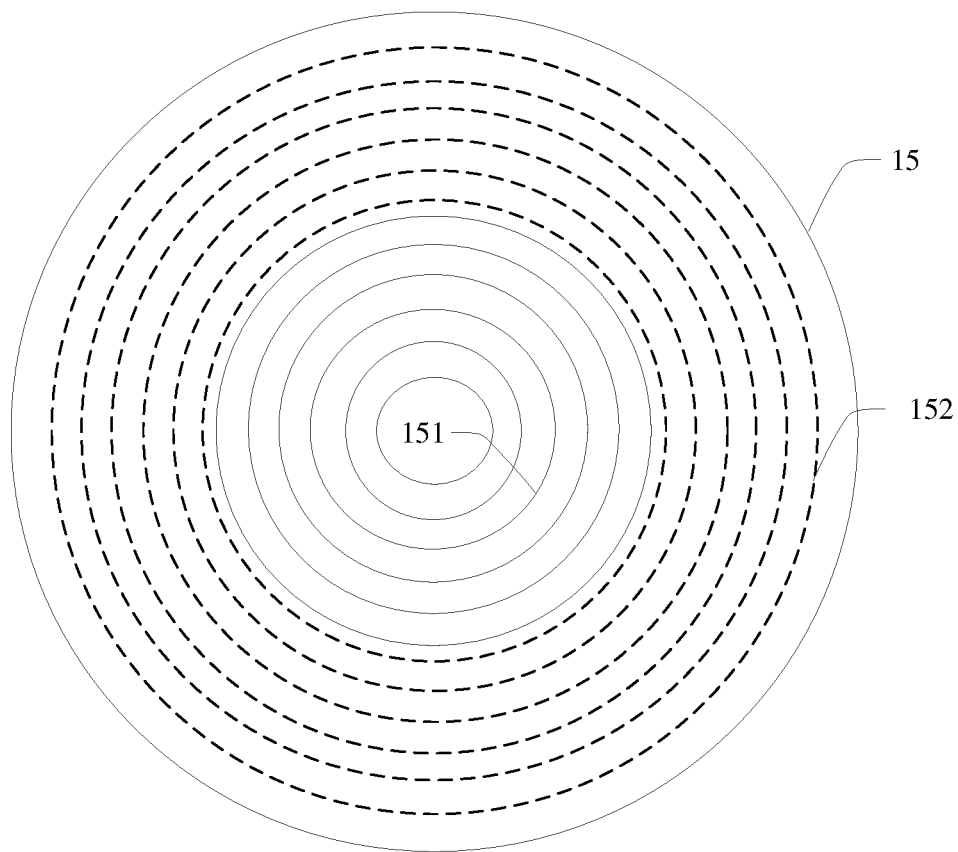
FIG. 10 is a schematic diagram of a structure of an optical film according to an embodiment of this application.

FIG. 10 is a schematic diagram of a structure of an optical film 15 according to an embodiment of this application. Middle solid line parts show vertex angles of the plurality of first light guide portions 151, and dashed line parts around the solid line parts show vertex angles of the plurality of second light guide portions 152. In this embodiment, the heart rate detection module 10 includes one light source 12, a plurality of optical receivers 13, and one light blocking portion 14. During application, on a side of the light source 12, the first light guide portion 151 filters interference light that is emitted from the light source 12 into the optical film 15 at a relatively large incident angle; and on a side of the optical receiver 13, the second light guide portion 152 filters interference light that is emitted to each optical receiver 13 at a relatively large angle after being reflected in the optical film 15, interference light that is emitted into the optical film 15 at a relatively large angle after being reflected from another tissue of a detection part 30, and the like. It should be noted that, the foregoing "side of the light source 12" means a side that is of the light blocking portion 14 and that is close to the light source 12 with the light blocking portion 14 as a boundary; and the foregoing "side of the optical receiver 13" means a side that is of the light blocking portion 14 and that is close to the optical receiver 13 with the light blocking portion 14 as a boundary. Therefore, in the heart rate detection module 10 in the foregoing embodiment, not only a phenomenon of an optical crosstalk that is transmitted from the light source 12 to each optical receiver 13 through the optical film 15 can be reduced, but also the interference light reflected from the detection part 30 can be filtered, so that impact of the interference light on receiving effective light by each optical receiver 13 can be better reduced, and accuracy of heart rate detection performed by the heart rate detection module 10 can be increased.

In a specific embodiment, each first light guide portion 151 may further meet: 60%≤x1/(x1+y1)≤85%, a width d1 (that is, d1=x1+y1) of each first light guide portion 151 may meet: 20 µm≤d1≤50 µm, and a height h1 of each first light guide portion 151 may meet: 20 µm≤h1≤40 µm; and each second light guide portion 152 may further meet: 15%≤x2/(x2+y2)≤40%, a width d2 (that is, d2=x2+y2) of each second light guide portion 152 may meet: 20 µm≤d2≤50 µm, and a height h2 of each second light guide portion 152 may meet: 20 µm≤h2≤40 µm. In the following Table 1, the optical film 15 is simulated by using an example in which an optical film 15 has a plurality of first light guide portions 151 and a plurality of second light guide portions 152 with a width of 30 µm (that is, d1=d2=30 µm). It can be seen from Table 1 that, in a case of the same width, as y1 and x2 gradually decrease, in other words, as the vertex angle of the first light guide portion 151 and the vertex angle of the second light guide portion 152 get closer to the light blocking portion 14, a value of transmitted light and a value of transmittance gradually increase. That is, the optical film 15 can also maintain relatively good transmittance performance when the optical film 15 has a function of filtering interference light.

TABLE 1

| x1 (μm)/y1 (μm) | x2 (μm)/y2 (μm) | Transmitted light | Leaked light | Transmittance |
|---|---|---|---|---|
| 25/5 | 5/25 | 9.82E−04 | 3.75E−05 | 67.13% |
| 24/6 | 6/24 | 9.55E−04 | 2.34E−05 | 66.18% |
| 23/7 | 7/23 | 9.65E−04 | 3.77E−05 | 65.92% |
| 22/8 | 8/22 | 9.50E−04 | 3.15E−05 | 65.26% |
| 21/9 | 9/21 | 8.67E−04 | 1.97E−05 | 60.20% |
| 20/10 | 10/20 | 8.32E−04 | 1.72E−05 | 57.93% |
| 19/11 | 11/19 | 8.30E−04 | 8.00E−05 | 53.29% |

Figure 11:
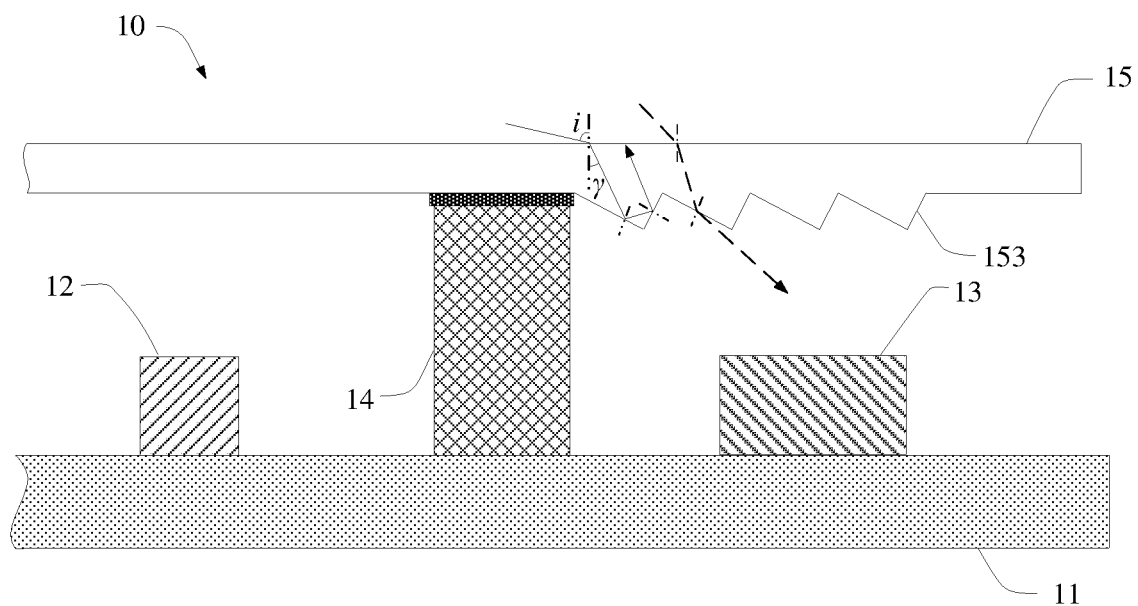
FIG. 11 is another locally enlarged schematic diagram of a heart rate detection module according to an embodiment of this application.

FIG. 11 is a schematic diagram of another structure of a heart rate detection module 10 according to an embodiment of this application. As shown in FIG. 11, for example, the heart rate detection module 10 includes one light source 12, one optical receiver 13, and one light blocking portion 14. In this embodiment, the light filtering portion 150 includes a plurality of third light guide portions 153. Specifically, the third light guide portion 153 is disposed close to the optical receiver 13, that is, the third light guide portion 153 is located on a side that is of the light blocking portion 14 and that is close to the optical receiver 13. The third light guide portion 153 is configured to guide, towards a direction deviating from the optical receiver 13, interference light that passes through an optical film 15, to reduce interference on receiving effective light by the optical receiver 13. The interference light may include light reflected from another tissue of a detection part 30, and light that is emitted from the light source 12 into the optical film 15 and that is emitted to the optical receiver 13 after being totally reflected in the optical film 15.

Figure 12:
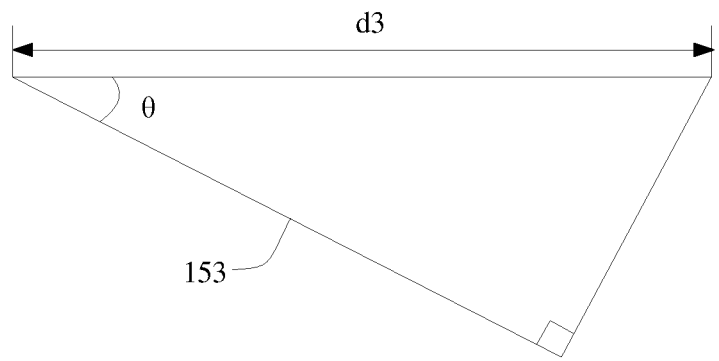
FIG. 12 is a schematic sectional view of a third light guide portion according to an embodiment of this application.

As shown in FIG. 11 again, in a specific embodiment, a section that is of each third light guide portion 153 and that is along a direction perpendicular to the optical film 15 is a right triangle. FIG. 12 is a schematic sectional view of a third light guide portion 153 according to an embodiment of this application. As shown in FIG. 12, a right angle of the triangle is downward, an edge opposite to the right angle is a bottom edge, and an angle θ is an internal angle (an internal angle on a left side shown in FIG. 12) that is of the third light guide portion 153 and that is close to the light source 12.

The following describes this embodiment in detail. As shown in FIG. 11, for example, a refractive index of the optical film 15 is 1.5. It is expected that a light beam reflected from a detection part 30 and emitted into the optical film 15 at an incident angle i≥50° is to be filtered. The incident angle i is an incident angle at which light is emitted into the optical film 15 from a surface of a side that is of the optical film 15 and that is away from a substrate 11. When the incident angle i is 50°, according to the Snell's Law sini/sin γ=1.5, where γ is a refraction angle at which light is emitted into the optical film 15 from the surface of the side that is of the optical film 15 and that is away from the substrate 11, it may be calculated that the refraction angle γ of the light in the optical film 15 is 30.71°. Because the third light guide portion 153 is a right triangle, incident angles of the light beam at interfaces of right-angle edges of the third light guide portion 153 are respectively (30.71°+θ) and (59.29°−θ). For example, when the angle θ is designed as 14.29°, both the incident angles of the light at the interfaces of the right-angle edges are 45°, and are greater than a total reflection angle 42° of the optical film 15 and air. Therefore, interference light may be reflected out of the optical film 15 and deviate from the optical receiver 13.

Figure 13:
FIG. 13 is a schematic diagram of transmittance of an optical film according to an embodiment of this application.

FIG. 13 is a schematic diagram of transmittance of the optical film 15 of the foregoing structure. It should be noted that a negative sign "−" means that when light is emitted to an interface, an incident angle is located on a side (shown by the incident angle i in FIG. 11) that is of a normal line (shown by a dotted line in FIG. 11) and that is closer to the light source 12 (as shown by the incident angle i in FIG. 11). In FIG. 13, changing from a negative angle to a positive angle means that an incident angle changes from a left side of the normal line to a right side of the normal line. It should be noted that the "incident angle" in this embodiment of this application includes an incident angle used when light is emitted from the light source 12 to the optical film 15, an incident angle used when light is reflected from the detection part 30 to the optical film 15, an incident angle used when light is totally reflected in the optical film 15, and an incident angle used when light is emitted to the optical receiver 13 in the optical film 15. Therefore, it may be understood that an angle of the incident angle in this embodiment of this application is negative. It can be seen from FIG. 13 that, as a range of the incident angle changes from −85° to −45°, the transmittance gradually increases and then slowly decreases; and as the range of the incident angle changes from −45° to 85°, the transmittance gradually increases again and then slowly decreases. As shown in FIG. 7, it can be learned that another tissue (for example, a skin surface layer 04) of the detection part 30 is closer to the heart rate detection module 10, and an incident angle of light reflected by the another tissue is larger when the light is emitted into the optical film 15. However, pulsating blood 01 is farther from the heart rate detection module 10, and an incident angle of light reflected by the pulsating blood 01 is smaller when the light is emitted into the optical film 15. Therefore, it may be considered that a light beam that is reflected by the detection part 30 and that is emitted into the optical film 15 at an incident angle of 30° to 60° may be used as interference light for filtering. In this case, the angle θ meets: 5°≤θ≤30°.

In some embodiments of this application, a width of the third light guide portion 153 is a length of a projection of the third light guide portion 153 on the optical film 15, for example, the length d3 of the bottom edge shown in FIG. 12. Similar to the first light guide portion 151 and the second light guide portion 152, to enable the third light guide portion 153 to have a relatively good effect of filtering interference light and facilitate manufacturing and processing, d3 may meet: 20 μm≤d3≤50 μm.

In this embodiment of this application, the light filtering portion 150 may be any combination of one or more first light guide portions 151, one or more second light guide portions 152, and one or more third light guide portions 153. For example, the light filtering portion 150 includes only one or more first light guide portions 151, or includes only one or more second light guide portions 152, or includes only one or more third light guide portions 153. Alternatively, the light filtering portion 150 may include one or more first light guide portions 151 and one or more third light guide portions 153. Alternatively, the light filtering portion 150 may include one or more first light guide portions 151 and one or more second light guide portions 152. Alternatively, the light filtering portion 150 may include one or more second light guide portions 152 and one or more third light guide portions 153. Alternatively, the light filtering portion 150 may include one or more first light guide portions 151, one or more second light guide portions 152, one or more third light guide portions 153.

In addition, the light filtering portion 150 may be disposed based on a location of each optical receiver 13. For example, the light filtering portion 150 includes a plurality of first light guide portions 151 and a plurality of second light guide portions 152. In a specific embodiment, the heart rate detection module 10 includes eight optical receivers 13 distributed in a ring, and the light filtering portion 150 includes eight first light guide portions 151 and eight second light guide portions 152, the eight first light guide portions 151 and the eight second light guide portions 152 are respectively disposed along the light blocking portion 14 in a one-to-one correspondence with each optical receiver 13. In addition, the plurality of first light guide portions 151 and the plurality of second light guide portions 152 may also be disposed based on a specific shape of the light blocking portion 14. For example, in another specific embodiment, the heart rate detection module 10 includes one light blocking portion 14 that is of a ring-shaped structure, and the light filtering portion 150 includes six first light guide portions 151 and six second light guide portions 152 that are separately arranged in a ring. As shown in FIG. 9 and FIG. 10, the six first light guide portions 151 are disposed on a side of the light source 12, and the six second light guide portions 152 are disposed on a side of the optical receiver 13. In still another specific embodiment, the plurality of first light guide portions 151 and the plurality of second light guide portions 152 may further be arranged threadedly.

In this embodiment of this application, the light filtering portion 150 may be a part of the optical film 15, or may be an independent component fastened on a surface of the optical film 15 by using an adhesive or the like. In another embodiment, the light filtering portion 150 may further be of another structure. For example, in some embodiments, the light filtering portion 150 may be a light absorption coating (for example, an ink coating) disposed on the surface of the optical film 15. None of a thickness, an angle, a shape, a type, and the like of the coating is limited. Details are not listed one by one in this application.

The optical film 15 may be any light transmission film layer such as a prism, a lens, or a scattering film. A specific layer structure of the optical film 15 is not limited in this embodiment of this application. The optical film 15 may be an optical film of a one-layer structure, or may be an optical film of a multi-layer structure. In comparison, using the optical film of the one-layer structure can reduce a manufacturing procedure of cutting and attaching the optical film 15, thereby reducing assembly difficulty of the heart rate detection module 10.

Figure 14:
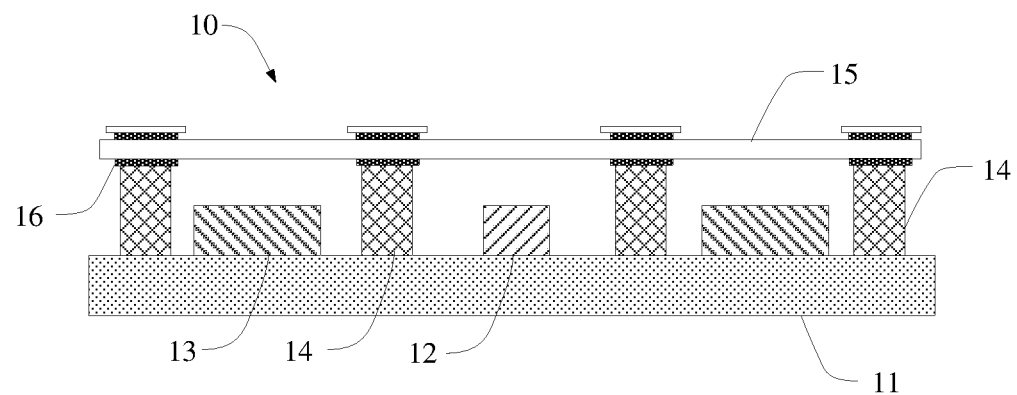
FIG. 14 is a schematic diagram of still another sectional structure of a heart rate detection module according to an embodiment of this application.
Figure 15:
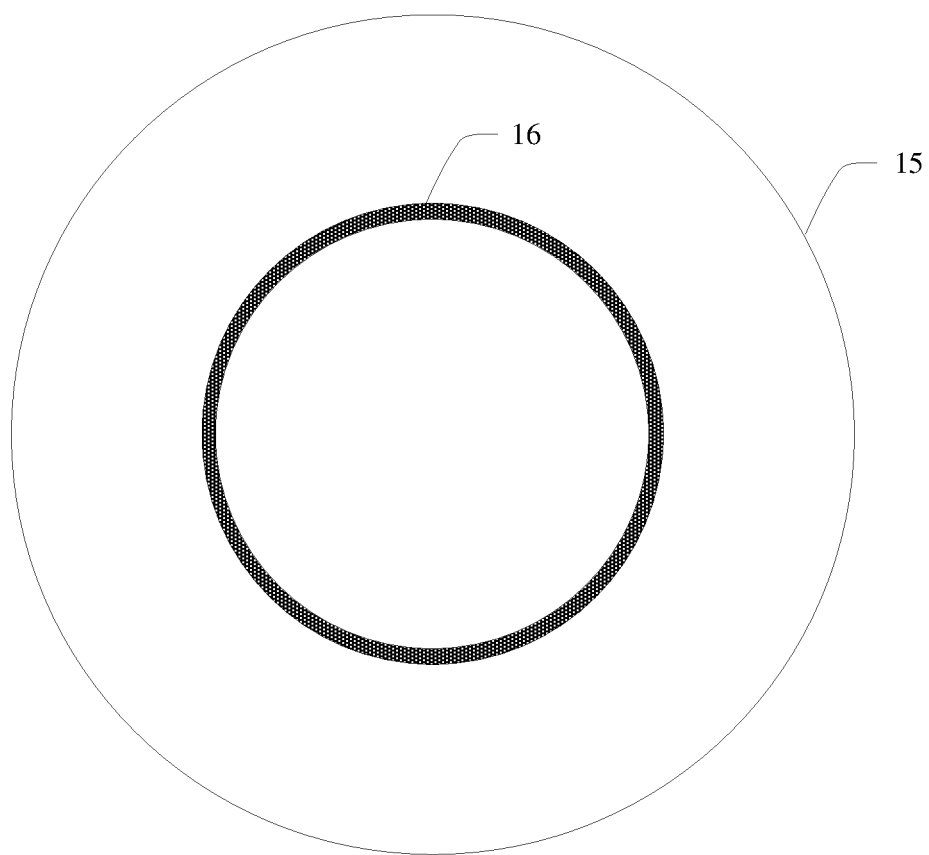
FIG. 15 is a schematic diagram of another structure of an optical film according to an embodiment of this application.

FIG. 14 is a schematic diagram of still another sectional structure of a heart rate detection module 10 according to an embodiment of this application. As shown in FIG. 14, for example, the heart rate detection module 10 includes one light source 12, a plurality of optical receivers 13 (FIG. 14 shows only two optical receivers 13 as an example), and two light blocking portions 14. In this embodiment, a light shield layer 16 corresponding to a location of the light blocking portion 14 is disposed on a surface of an optical film 15 (or as shown in FIG. 2). In other words, the light shield layer 16 does not affect propagation of a light beam emitted from the light source 12 to a detection part 30 and a light beam emitted to each optical receiver 13 after being reflected from the detection part 30. The light shield layer 16 may reduce interference light. For example, some of light emitted to the optical film 15 at a relatively large incident angle is shielded by the light shield layer 16, so that the light is not emitted to each optical receiver 13. The light shield layer 16 may be a light absorption coating coated on the surface of the optical film 15. For example, a light shield layer 16 shown in FIG. 15 is an ink coating. Certainly, the light shield layer 16 may alternatively be a dark-color adhesive used for bonding the optical film 15. The light shield layer 16 may be disposed on a surface of a side of the optical film 15, or may be disposed on surfaces of two sides of the optical film 15. This is not further described in this embodiment of this application.

In this embodiment, the plurality of optical receivers 13 surround the light source 12, the two light blocking portions 14 are ring-shaped, one ring-shaped light blocking portion is disposed between the light source 12 and each optical receiver 13, and the other ring-shaped light blocking portion is disposed on a periphery of the optical receivers 13, so that the light source 12 and the optical receivers 13 are separately isolated by the light blocking portion 14 in respective space, and light emitted by the light source 12 or external light cannot directly irradiate each optical receiver 13. In other words, each optical receiver 13 can receive only a light beam that passes through the optical film 15. In this way, impact of other interference light on receiving effective light by the receiver 15 can be more effectively reduced, and detection accuracy of the heart rate detection module 10 in this instance of this application is further increased.

Figure 16:
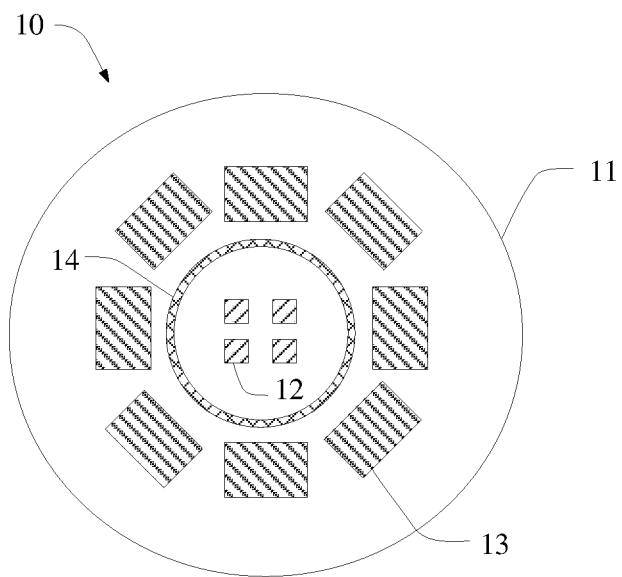
FIG. 16 is a schematic diagram of another structure of a heart rate detection module according to an embodiment of this application.
Figure 17:
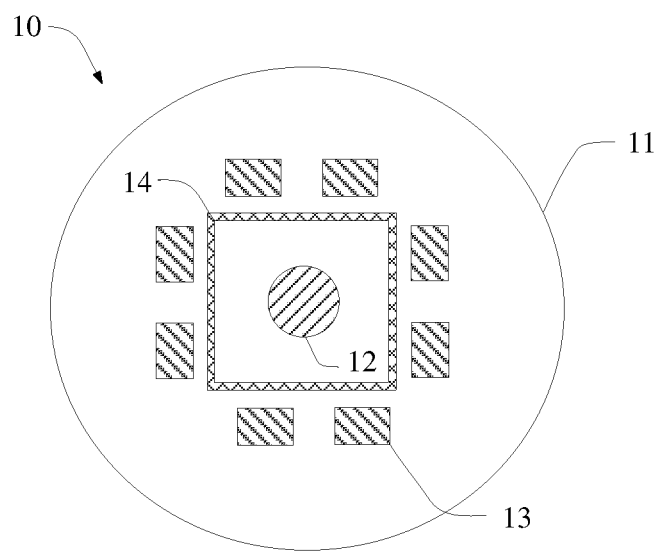
FIG. 17 is a schematic diagram of another structure of a heart rate detection module according to an embodiment of this application.
Figure 18:
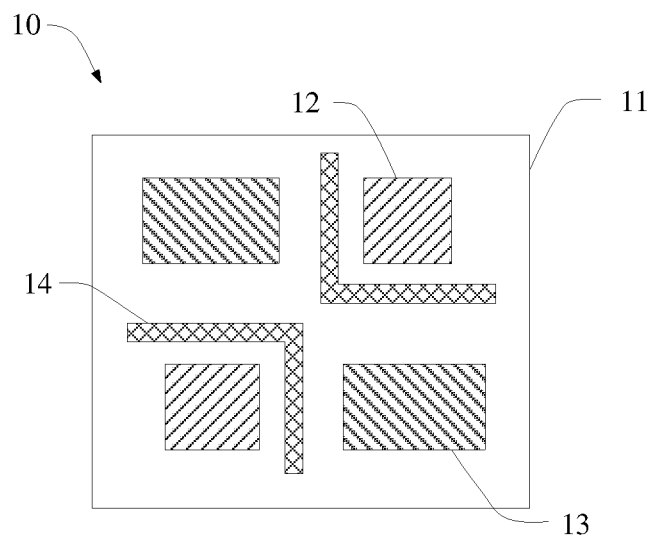
FIG. 18 is a schematic diagram of another structure of a heart rate detection module according to an embodiment of this application.

FIG. 16 to FIG. 18 are schematic diagrams of different structures of a heart rate detection module 10 according to embodiments of this application, and show different layouts of one or more light sources 12, a plurality of optical receivers 13, and one or more light blocking portions 14 on a substrate 11. As shown in FIG. 16, eight optical receivers 13 equidistantly surround, in a ring shape, a periphery of the four light sources 12 arranged in a rectangular shape, and one light blocking portion 14 is disposed in a ring shape between the light source 12 and the optical receivers 13, so that light emitted by the light source 12 can be emitted only through an optical film 15. As shown in FIG. 17, the light source 12 may be a circular LED device, eight optical receivers 13 may be equidistantly disposed in a rectangular shape around the LED device, and one light blocking portion 14 is disposed in a rectangular shape between the light source 12 and the optical receivers 13. In some other embodiments of this application, the plurality of light sources 12 may alternatively be disposed around one or more optical receivers 13. For example, in a specific embodiment, eight light sources 12 surround, in a ring shape, one optical receiver 13. Alternatively, in another specific embodiment, as shown in FIG. 18, in a rectangular structure, two optical receivers 13 are diagonally disposed, and two light sources 12 are disposed on two sides of the two optical receivers 13, to form a diagonal. It may be understood that, in embodiments of this application, quantities and arrangement forms of light sources 12, optical receivers 13, and light blocking portions 14 are not limited. For example, light sources 12, optical receivers 13, and light blocking portions 14 are disposed in a ring, a polygon, or a diagonal, and may be specifically disposed based on a size or a shape of an electronic device, or a specific preference or requirement of a user.

Figure 19:
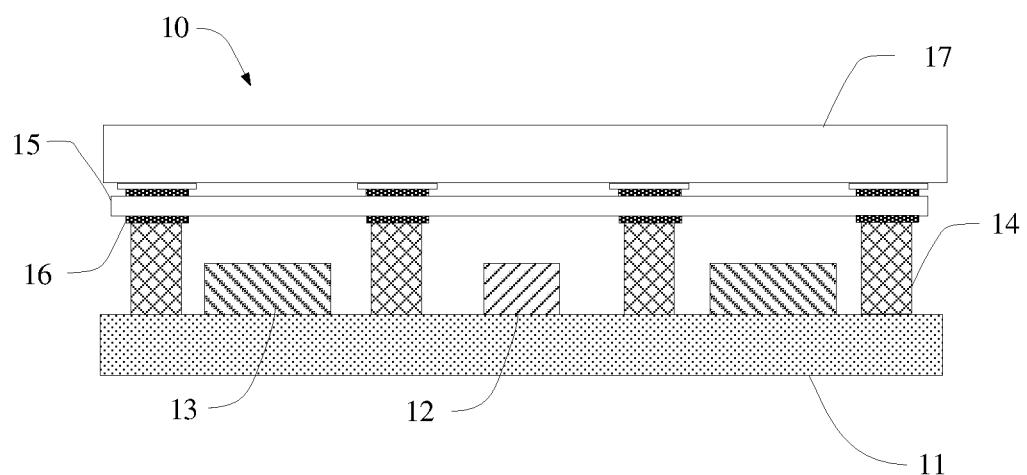
FIG. 19 is a schematic diagram of another sectional structure of a heart rate detection module according to an embodiment of this application.

FIG. 19 is a schematic diagram of another sectional structure of a heart rate detection module 10 according to an embodiment of this application. As shown in FIG. 19, the heart rate detection module 10 may further include a cover 17. The cover 17 may protect other devices of the heart rate detection module 10, to prevent the devices from being damaged due to collision in a transportation process. The cover 17 may be made of a transparent material such as glass, polycarbonate (Polycarbonate, PC), or polymethyl methacrylate (polymethyl methacrylate, PVC). The transparent materials are not listed one by one in this application. The cover 17 and the optical film 15 may be assembled in a bonding manner. For example, in a specific embodiment, the cover 17 and the optical film 15 may be bonded by using a dark-color adhesive. The dark-color adhesive corresponds to locations of one or more light blocking portions 14. In this way, a propagation path of effective light in the heart rate detection module 10 is not affected, and a surface structure of the optical film 15 may further be protected. In addition, the optical film 15 and the light blocking portion 14 may also be assembled in a bonding manner. Such an assembly manner is convenient for manufacturing.

Figure 20:
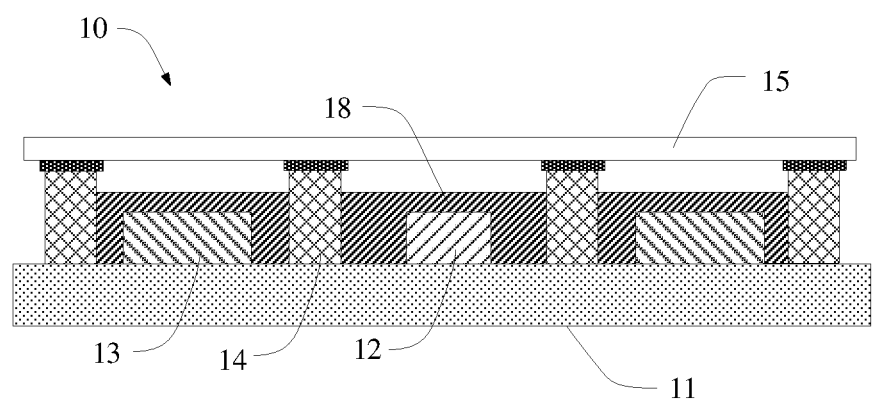
FIG. 20 is a schematic diagram of another sectional structure of a heart rate detection module according to an embodiment of this application.
Figure 21:
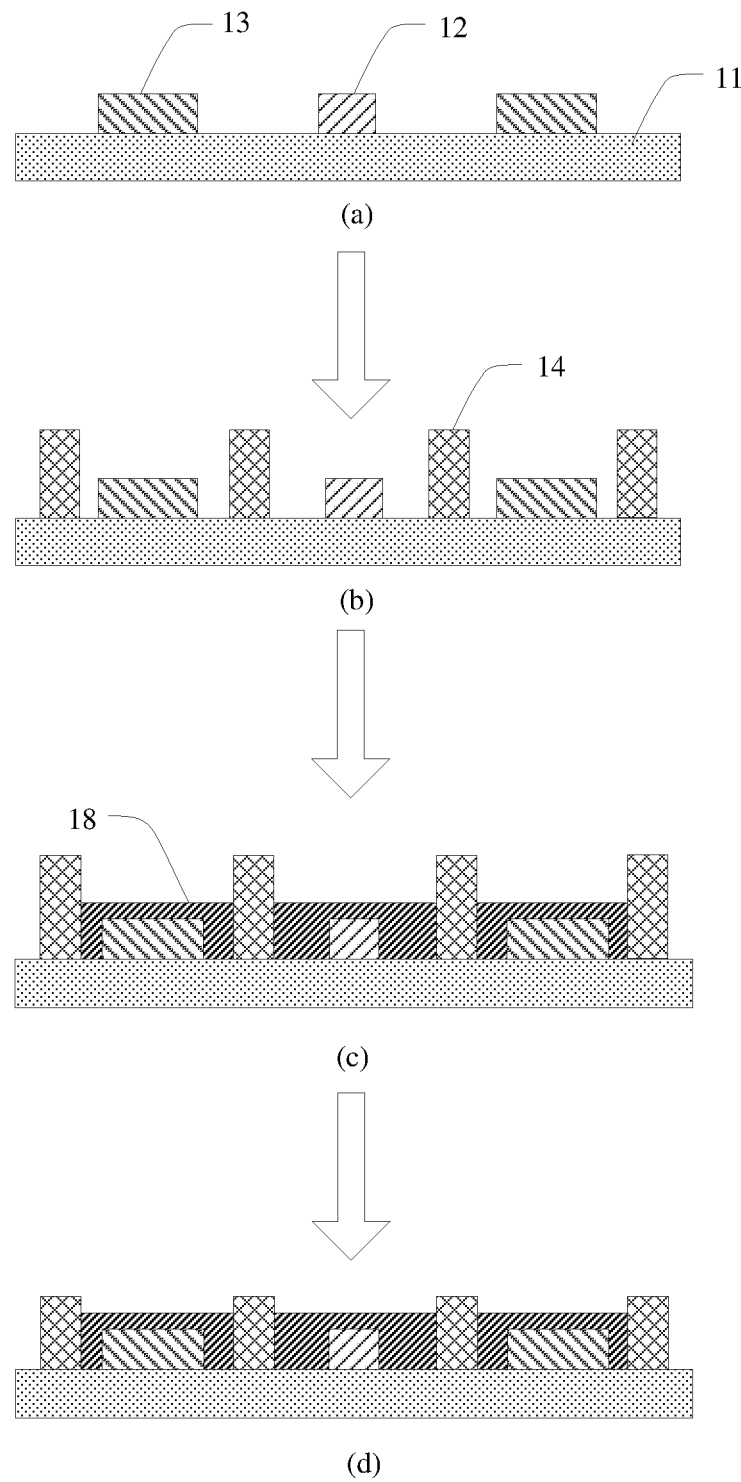
FIG. 21 is a schematic diagram of a packaging procedure of a heart rate detection module according to an embodiment of this application.

FIG. 20 is a schematic diagram of another sectional structure of a heart rate detection module 10 according to an embodiment of this application. As shown in FIG. 20, in this embodiment of this application, the heart rate detection module 10 may further include a packaging layer 18 located between a substrate 11 and an optical film 15. In this embodiment, for example, the heart rate detection module 10 includes one light source 12, a plurality of optical receivers 13 (FIG. 14 shows only two optical receivers 14 as an example), and two light blocking portions 14. In some embodiments of this application, the packaging layer 18 may package the light source 12 and the optical receivers 13, as shown in (a) to (d) in FIG. 21. First, the light source 12 and each optical receiver 13 are disposed on the PCB substrate 11. The light source 12 and an electrode of each optical receiver 13 may be electrically connected to the substrate 11 by using a bonding line, as shown in (a) in FIG. 21. Next, the light blocking portion 14 is disposed on the substrate 11 through welding, bonding, or the like, to form an inner-ring light blocking portion around the light source 12 and an outer-ring light blocking portion around the optical receivers 13, as shown in (b) in FIG. 21. Then, a packaging material is filled, through glue injection and formation (for example, through glue dripping), into space formed by the light blocking portion 14 and the substrate 11, and the filled packaging material is cured to form the packaging layer 18. In this way, the light source 12, each optical receiver 13, the bonding line, and another device are packaged, as shown in (c) in FIG. 21. Finally, an entire device formed through packaging is cut into an expected size through laser cutting, as shown in (d) in FIG. 21. In such an integrated packaging process, the light source 12 and each optical receiver 13 may use a chip in a form of a bare die. In this way, design space of the heart rate detection module 10 can be fully used, to reduce a thickness of the entire heart rate detection module 10. The packaging layer 18 may further protect the chip and a circuit, to reduce damage caused by collision occurred during transportation, and prevent particles such as dust from entering the heart rate detection module 10, thereby further improving reliability of heart rate detection performed by the heart rate detection module 10. In addition, because the light source 12 and each optical receiver 13 are packaged, a cleanliness requirement on a processing environment may be reduced in a subsequent manufacturing process, to reduce manufacturing costs.

In a specific embodiment, when an entire optical film is used, no requirement may be made on a height of the light blocking portion 14 and a height of the packaging layer 18. Therefore, the cutting step shown in (c) in FIG. 21 may be omitted, to reduce difficulty of the manufacturing process of the heart rate detection module 10.

In addition, in some other embodiments of this application, devices such as one or more light sources 12, one or more light blocking portions 14, and one or more optical receivers 13 may alternatively be first packaged into an independent device, and then the independent device is installed on the substrate 11 and is electrically connected to the substrate 11.

Figure 22:
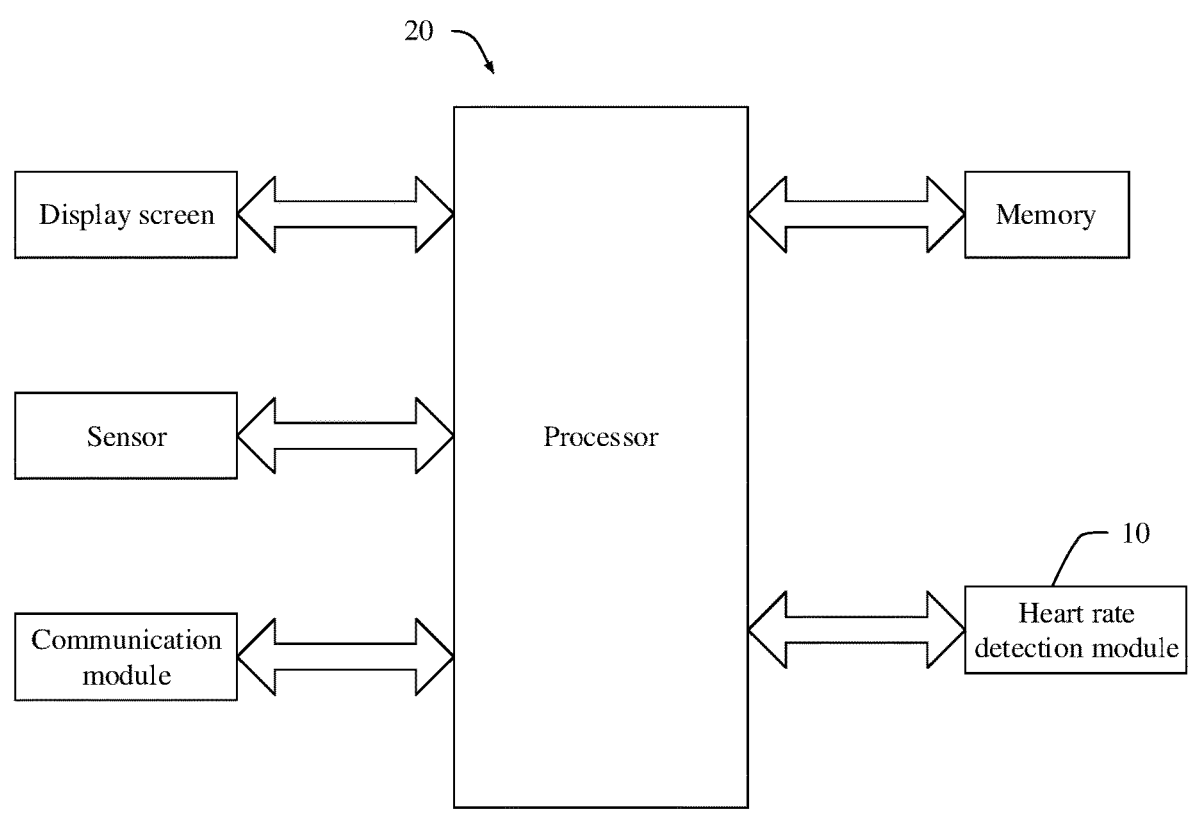
FIG. 22 is a schematic diagram of a structure of an electronic device according to an embodiment of this application.

As shown in FIG. 22, this application further provides an electronic device 20, and the electronic device 20 includes an electronic device body and the heart rate detection module 10 in any one of the foregoing embodiments. FIG. 22 is a block diagram of an electronic device 20. Aspects of the heart rate detection module 10 configured to detect a heart rate may be implemented on the electronic device 20. The electronic device 20 may be provided to a user in a form of a plurality of devices or in a form of a single device, such as a smartphone, a wearable device, or a heart rate meter. The wearable device may be a smartwatch, a smart band, a helmet, smart clothing, or another accessory. Details are not described one by one in this application. In a process in which the heart rate detection module 10 obtains an optical signal, a light filtering portion 150 of the heart rate detection module 10 may filter interference light emitted to each optical receiver 13, to provide a signal-to-noise ratio of the obtained heart rate signal, thereby implementing heart rate detection with relatively high accuracy.

As shown in FIG. 22, in some embodiments of this application, the electronic device 20 may further include a processor, and modules such as a memory, a sensor, a communication module, and a display screen that are electrically connected to the processor separately. The heart rate detection module 10 is electrically connected to the processor. In this embodiment, the heart rate detection module 10 is configured to: obtain physiological parameters such as a dynamic heart rate and a blood oxygen saturation level of a human body, and transmit the parameters to the processor. The memory is configured to store program instructions and data that is obtained during program execution. The sensor may be an acceleration sensor, a gyro sensor, an ambient light sensor, or another type, and is configured to sense an environment in which the electronic device 20 is located and a motion status of the sensor. The communication module has communication functions such as Wi-Fi, Bluetooth, and NFC (Near Field Communication, near field communication), and is configured to: transfer data to the processor or receive a command from the processor. The display screen may provide a human-computer interaction interface to present various information to a user. In addition, the display screen may alternatively be a touchscreen, and is configured to implement a touch input. The processor is configured to: execute the program instructions, perform control, management, and signal processing on an entire system of the electronic device 20, process the signal obtained by the heart rate detection module 10, and generate the physiological parameter of the user.

In this embodiment of this application, the heart rate detection module 10 is detachably installed in the electronic device body in different manners, for example, through a threaded connection and clamping. This is not limited in this application. Such a design can facilitate maintenance of the electronic device 20 and replacement of the heart rate detection module 10. For example, after the heart rate detection module 10 uses one or more integrated light sources 12, one or more optical receivers 13, and one or more light blocking portions 14 that are integrally packaged, a light shield layer 16 and a cover 17 are sequentially bonded to a packaging layer 18, and are finally assembled into the heart rate detection module 10. The heart rate detection module 10 may be installed in the electronic device body as an independent integrated device, so that the heart rate detection module 10 is repaired or replaced after being directly detached from the electronic device body. In addition, an interface may be disposed on a substrate 11 of the heart rate detection module 10, and the interface may be connected to the electronic device 20.

A specific embodiment in which the electronic device 20 includes a smartwatch and a smartphone electrically connected to the smartwatch is used below to describe a process in which the electronic device 20 is applied to heart rate detection.

In this embodiment, the heart rate detection module 10 in this embodiment of this application is disposed inside the smartwatch, and is located at a bottom portion of a watch face of the smartwatch. Specifically, when a user wears the smartwatch on a wrist, one side of the optical film 15 of the heart rate detection module 10 is close to the wrist of the user. In this case, a detection part 30 is a part at which the wrist of the user comes into contact with the bottom portion of the watch face of the smartwatch. After a heart rate detection function of the smartwatch is enabled, the one or more light sources 12 of the heart rate detection module 10 emit light beams, and some light beams reach the detection part 30 after passing through the optical film 15. Light reflected by pulsating blood 01 of the detection part 30 passes through the optical film 15 again and is emitted to the one or more optical receivers 13. After receiving an optical signal, each optical receiver 13 transmits data of the optical signal to a processor of the smartwatch by using a communication module. The processor processes and analyzes the data, to finally obtain a heart rate status of the user. The heart rate status is displayed to the user by using the display screen. In a process of obtaining the optical signal, interference light emitted to each optical receiver 13 may be filtered by the light filtering portion 150, so that a proportion of effective light in the optical signal can be effectively increased, and a signal-to-noise ratio of the heart rate detection module 10 and detection accuracy of the electronic device 20 can be increased.

The terms used in the foregoing embodiments are merely intended to describe particular embodiments, but are not intended to limit this application. The terms "one", "a", "the", "the foregoing", "this", and "the one" in singular forms used in this specification and the appended claims of this application are also intended to include expressions such as "one or more", unless otherwise specified in the context clearly.

Reference to "one embodiment", "some embodiments", or the like described in this specification means that a particular feature, structure, or characteristic described with reference to one or more embodiments is included in the one or more embodiments of this application. Therefore, statements such as "in an embodiment", "in another embodiment", "in some embodiments", "in some other embodiments", and "in other embodiments" that appear at different places in this specification do not necessarily mean referring to a same embodiment. Instead, the statements mean "one or more but not all of embodiments", unless otherwise specifically emphasized in another manner. The terms "include", "have", and their variants all mean "include but are not limited to", unless otherwise specifically emphasized in another manner.

The foregoing descriptions are merely specific implementations of this application, but are not intended to limit the protection scope of this application. Any variation or replacement readily figured out by a person skilled in the art within the technical scope disclosed in this application shall fall within the protection scope of this application. Therefore, the protection scope of this application shall be subject to the protection scope of the claims.

What is claimed is:

1. A heart rate detection module, comprising:
a substrate;
a light source disposed on the substrate;
an optical receiver disposed on the substrate at an interval from the light source;
a light blocking portion disposed on the substrate between the light source and the optical receiver; and
an optical film, wherein the optical film covers the light source, the optical receiver, and the light blocking portion, a light filtering portion is on a side of the optical film that faces the substrate, and the light filtering portion is configured to filter interference light emitted to the optical receiver;
wherein the light filtering portion comprises a first light guide portion between the light source and the light blocking portion, and the first light guide portion is configured to guide interference light that comes from the light source to deviate from the optical receiver; and
wherein a section of the first light guide portion that is along a direction perpendicular to the optical film is a triangle, and meets: x1>y1, wherein x1 is a length of a projection, on a surface of the optical film, of a side edge that is of the section of the first light guide portion and that is closest to the light source, and y1 is a length of a projection, on the surface of the optical film, of a side edge that is of the section of the first light guide portion and that faces away from the light source.

2. The heart rate detection module according to claim 1, wherein the first light guide portion meets 60%≤x1/(x1+y1)≤85%.

3. The heart rate detection module according to claim 1, wherein a height h1 of the section of the first light guide portion meets: 20 μm≤h1≤40 μm, and 20 μm≤x1+y1≤50 μm.

4. The heart rate detection module of claim 1, wherein the light filtering portion further comprises a second light guide portion between the optical receiver and the light blocking portion, and the second light guide portion is configured to guide interference light emitted from the optical film to deviate from the optical receiver.

5. The heart rate detection module of claim 4, wherein a section of the second light guide portion that is along a direction perpendicular to the optical film is a triangle, and meets: x2<y2, wherein x2 is a length of a projection, on a surface of the optical film, of a side edge that is of the section of the second light guide portion and that faces away from the optical receiver, and y2 is a length of a projection, on the surface of the optical film, of a side edge that is of the section of the second light guide portion and that faces the optical receiver.

6. The heart rate detection module according to claim 5, wherein the second light guide portion meets 15%≤x2/(x2+y2)≤40%.

7. The heart rate detection module according to claim 5, wherein a height h2 of the section of the second light guide portion meets: 20 μm≤h2≤40 μm, and 20 μm≤x2+y2≤50 μm.

8. The heart rate detection module of claim 1, wherein a light shield layer corresponding to the light blocking portion is disposed on a surface of the optical film.

9. The heart rate detection module of claim 1, wherein the optical film is an entire optical film.

10. The heart rate detection module of claim 1, wherein the light source, the light blocking portion, and the optical receiver are integrally packaged.

11. An electronic device, comprising:
an electronic device body; and
a heart rate detection module, comprising:
  a substrate;
  a light source disposed on the substrate;
  an optical receiver disposed on the substrate at an interval from the light source;
  a light blocking portion disposed on the substrate between the light source and the optical receiver; and
  an optical film, wherein the optical film covers the light source, the optical receiver, and the light blocking portion, a light filtering portion is on a side that is of the optical film that faces the substrate, and the light filtering portion is configured to filter interference light emitted to the optical receiver; and
wherein the heart rate detection module is configured to obtain a heart rate signal of a user;
wherein the light filtering portion comprises a first light guide portion between the light source and the light blocking portion, and the first light guide portion is configured to guide interference light that comes from the light source to deviate from the optical receiver; and
wherein a section of the first light guide portion that is along a direction perpendicular to the optical film is a triangle, and meets: $x1>y1$, wherein x1 is a length of a projection, on a surface of the optical film, of a side edge that is of the section of the first light guide portion and that is closest to the light source, and y1 is a length of a projection, on the surface of the optical film, of a side edge that is of the section of the first light guide portion and that faces away from the light source.

12. The electronic device according to claim 11, wherein the heart rate detection module is detachably connected to the electronic device body.

13. The electronic device according to claim 12, wherein the first light guide portion meets $60\% \leq x1/(x1+y1) \leq 85\%$.

14. The electronic device according to claim 13, wherein a height h1 of the section of the first light guide portion meets: $20\ \mu m \leq h1 \leq 40\ \mu m$, and $20\ \mu m \leq x1+y1 \leq 50\ \mu m$.

15. The electronic device of claim 11, wherein the light filtering portion further comprises a second light guide portion between the light blocking portion and the optical receiver, and the second light guide portion is configured to guide interference light emitted from the optical film to deviate from the optical receiver.

16. The electronic device of claim 15, wherein a section of the second light guide portion that is along a direction perpendicular to the optical film is a triangle, and meets: $x2<y2$, wherein x2 is a length of a projection, on a surface of the optical film, of a side edge that is of the section of the second light guide portion and that faces away from the optical receiver, and y2 is a length of a projection, on the surface of the optical film, of a side edge that is of the section of the second light guide portion and that faces the optical receiver.

17. The electronic device according to claim 15, wherein the second light guide portion meets $15\% \leq x2/(x2+y2) \leq 40\%$.

18. The electronic device according to claim 15, wherein a height h2 of a section of the second light guide portion meets: $20\ \mu m \leq h2 \leq 40\ \mu m$, and $20\ \mu m \leq x2+y2 \leq 50\ \mu m$.

19. The electronic device according to claim 11, wherein the light source, the light blocking portion, and the optical receiver are integrally packaged.

20. The electronic device according to claim 11, wherein a light shield layer corresponding to the light blocking portion is disposed on a surface of the optical film.

* * * * *